(12) United States Patent
Cook

(10) Patent No.: US 7,943,832 B2
(45) Date of Patent: May 17, 2011

(54) INBRED TOMATO LINE 1T247

(75) Inventor: Lisa Cook, Naples, FL (US)

(73) Assignee: Syngenta Participations AG, Basel (CH)

( * ) Notice: Subject to any disclaimer, the term of this patent is extended or adjusted under 35 U.S.C. 154(b) by 499 days.

(21) Appl. No.: 12/061,292

(22) Filed: Apr. 2, 2008

(65) Prior Publication Data

US 2008/0254179 A1   Oct. 16, 2008

Related U.S. Application Data

(60) Provisional application No. 60/922,766, filed on Apr. 10, 2007.

(51) Int. Cl.
*A01H 1/00* (2006.01)
*C07H 21/04* (2006.01)
*C07K 14/415* (2006.01)
*C12N 15/00* (2006.01)

(52) U.S. Cl. ............ 800/317.4; 435/468; 435/412; 435/418; 435/424; 530/370; 536/23.1; 800/260; 800/278; 800/300; 800/301; 800/302

(58) Field of Classification Search .......... 435/468, 435/412, 418, 424; 530/370; 536/23.1; 800/260, 800/278, 288, 300, 301, 302, 317.4
See application file for complete search history.

(56) References Cited

U.S. PATENT DOCUMENTS

PP5,171 P * 1/1984 Briggs

* cited by examiner

*Primary Examiner* — Phuong T Bui
(74) *Attorney, Agent, or Firm* — S. Matthew Edwards

(57) ABSTRACT

The present invention relates to a new and distinct inbred tomato lines and hybrids. This invention also relates to plants and seeds of such inbred tomato lines and hybrids, and to parts thereof. The invention also relates to methods for producing a tomato plant produced by crossing such inbred tomato lines and hybrids with themselves or other tomato plants.

17 Claims, No Drawings

US 7,943,832 B2

INBRED TOMATO LINE 1T247

FIELD OF THE INVENTION

The present invention relates to the field of agriculture, and to new and distinct inbred lines and hybrids of tomato (*Lycopersicon esculentum*), and to method of making and using such inbred lines and hybrids.

BACKGROUND OF THE INVENTION

The goal of plant breeding is to develop new, unique and superior cultivars. Theoretically, a breeder can generate billions of different genetic combinations via crossing, selfing and selection. A breeder has no direct control at the cellular level. Therefore, two breeders will never develop the same line, or even very similar lines, having precisely the same traits. Descriptions of breeding methods that are commonly used for different traits and crops, as well as specifically for tomato, can be found in one of several reference books (e.g., Allard, R. W. (1960) Principles of Plant Breeding; Simmonds, N. W. (1979) Principles of Crop Improvement; Sneep, J. et al., (1979) Tomato Breeding (p. 135-171) in: Breeding of Vegetable Crops, Mark J. Basset, (1986, editor), The Tomato crop: a scientific basis for improvement, by Atherton, J. G. & J. Rudich, (1986, editors); Plant Breeding Perspectives; Fehr, (1987) Principles of Cultivar Development—Theory and Technique).

The method chosen for breeding or selection depends on the mode of plant reproduction, the heritability of the trait(s) being improved, and the cultivar (i.c. variety) used commercially (e.g. F1 hybrid, or an open-pollinated variety). The complexity of the inheritance influences the choice of breeding method. One simple method of identifying a superior plant is to observe its performance relative to other experimental plants or to a widely grown standard cultivar, and to observe its performance in hybrid combinations with other plants. If single observations are inconclusive for establishing distinctness, observations in multiple locations and seasons provide a better estimate of its genetic worth. Proper testing and evaluation should detect any major faults and establish the level of superiority or improvement over current cultivars.

The development of commercial tomato hybrids requires the development of homozygous inbred parental lines. In breeding programs desirable traits from two or more germplasm sources or gene pools are combined to develop superior breeding lines. Desirable inbred or parent lines are developed by continuous selfing and selection of the best breeding lines, sometimes utilizing molecular markers to speed up the selection process.

Once the inbreds that give the best hybrid performance have been identified, the hybrid seed can be produced indefinitely, as long as the homogeneity and the homozygosity of the inbred parents is maintained. A single-cross hybrid is produced when two inbred lines are crossed to produce the F1 progeny. Much of the hybrid vigor exhibited by F1 hybrids is lost in the next generation (F2). Consequently, seed harvested from hybrid varieties is not used for planting stock.

There are numerous steps involved in the breeding and development of any new and novel, desirable plant germplasm with superior combining ability. Plant breeding begins with the analysis and definition of problems and weaknesses of the current germplasm, the establishment of program goals, and definition of specific breeding objectives. The next step is selection of germplasm that possess the traits to meet the program goals and the definition of the best breeding method to reach those goals. The objective is to combine in a single hybrid variety an improved combination of desirable traits from the parental germplasm. Important characteristics may include higher yield, better flavor, improved color and field holding ability, resistance to diseases and insects, tolerance to drought and heat, along with characteristics related to hybrid seed yields to lower the cost of hybrid seed production.

Tomato is a very important crop in all continents of the world. Several plant species associated with the *Solanum* group have been familiar to mankind since ancient times, and are of great agricultural importance. *Solanum* species have a general adaptation to variable climatic growing conditions. Tomato (*Lycopersicon esculentum* L.) belongs to the Solaneaceous family. All varieties in the species *esculentum* are self-pollinating. Most other species in the genus *Lycopersicon* are cross-pollinating. Cross-pollination is affected by insect vectors, most commonly by the honey- or bumblebees. Tomato, like most other *Lycopersicon* species, is highly variable. Variability in populations is desired for wide adaptation and survival. Tomato is adapted to warm summer growing conditions, but can also be grown in heated greenhouses under winter conditions. The introduction of hybrid cultivars in the 1950's provided a magnitude of benefits like increased yield, better holding ability, adaptation to expanded growing seasons through the use of protected cultivation and improved disease resistance, which resulted in large-scale production of tomato as a commercial crop.

The goal in tomato breeding is to make continued improvements in hybrid tomato yields, in other horticultural characteristics, as well as in quality traits, in order to meet continuous demands for better tomato cultivars in different growing regions of the world.

SUMMARY OF THE INVENTION

The present invention discloses new and distinct inbred tomato lines and hybrids of tomato (*Lycopersicon esculentum*). The present invention also discloses methods of making and using such inbred lines and hybrids.

In one embodiment, the present invention discloses a new and distinct inbred tomato line, designated 1T247. In one embodiment, the present invention relates to a new and distinct inbred tomato line, designated 1T246. This invention also discloses seeds of inbred tomato lines 1T247 and 1T246, plants of inbred tomato lines 1T247 and 1T246, and parts of said plants, such as pollen, ovule or fruit. The present invention also discloses methods for producing a tomato plant produced by crossing a plant of inbred line 1T247 or 1T246 with itself or another tomato line.

This invention also relates to methods for producing other inbred tomato lines derived from inbred tomato line 1T247 or 1T246, and to the inbred tomato lines derived by the use of those methods. This invention further relates to hybrid tomato seeds and plants produced by crossing inbred tomato line 1T247 or 1T246 with another tomato line. In particular, this invention further relates to hybrid tomato seeds and plants produced by crossing inbred tomato line 1T247 or 1T246 with line FLA 7804 to obtain hybrid Finishline and hybrid Redline [4971], respectively.

In one embodiment, this invention also discloses seeds of tomato hybrids Finishline and Redline [4971], plants of tomato hybrids Finishline and Redline [4971], and parts of said plants, such as pollen, ovule or fruit. The present invention also discloses methods for producing a tomato plant comprising crossing tomato hybrids Finishline and Redline [4971] with itself or another tomato line.

The invention further discloses method of producing seed of a plant of the present invention comprising crossing an inbred line or hybrid of the present invention with itself or with another line or hybrid, and seed produced by such method. The invention also discloses methods of vegetatively propagating a plant of the present invention, and to plants produced by such methods. This invention also methods for producing a fruit of a tomato plant of the present invention and to fruits produced by such methods.

A tomato plant of the invention may further comprise a cytoplasmic factor or other factor that is capable of conferring male sterility. Male sterility may also be provided by nuclear genes such as the recessive ms gene.

In another aspect, the present invention provides regenerable cells for use in tissue culture. The tissue culture will preferably be capable of regenerating plants having the physiological and morphological characteristics of the foregoing tomato plants, and of regenerating plants having substantially the same genotype as the foregoing tomato plants. Preferably, the regenerable cells in such tissue cultures will be embryos, protoplasts, meristematic cells, callus, pollen, leaves, anthers, stems, petioles, roots, root tips, fruits, seeds, flowers, cotyledons, hypocotyls or the like. Still further, the present invention provides tomato plants regenerated from the tissue cultures of the invention.

In another aspect, the present invention provides for single gene converted plants of inbred tomato lines 1T247 and 1T246, or hybrids Finishline and Redline [4971]. The single transferred gene may preferably be a dominant or recessive allele. Preferably, the single transferred gene will confer such trait as male sterility, herbicide resistance, insect resistance, resistance for bacterial, fungal, or viral disease, male fertility, improved harvest characteristics, enhanced nutritional quality, improved processing characteristics. The single gene may be a naturally occurring tomato gene or a transgene introduced through genetic engineering techniques. The present invention also discloses methods for producing a tomato plant containing in its genetic material one or more transgenes and to the transgenic tomato plants produced by that method.

The invention further provides methods for developing tomato plant in a tomato plant breeding program using plant breeding technique including recurrent selection, backcrossing, pedigree breeding, restriction fragment length polymorphism enhanced selection, genetic marker enhanced selection and transformation. Seeds, tomato plant, and parties thereof produced by such breeding methods are also part of the invention.

Definitions

In the description and tables that follow, a number of terms are used. The terms are used to provide a clear understanding of the specifications and are used in accordance with the terminology defined in the UPOV Technical Guidelines for tomato (TG/4417), which is incorporated herein by reference in its entirety. The following definitions are also provided:

Allele. The allele is any of one or more alternative form of a gene, all of which alleles relates to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid F1 with one of the parental genotype of the F1 hybrid.

Regeneration. Regeneration refers to the development of a plant from tissue culture.

Single gene converted. Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Soluble Solids. Soluble solids refers to the percent of solid material found in the fruit tissue, the vast majority of which is sugars. Soluble solids are directly related to finished processed product yield of pastes and sauces. Soluble solids are estimated with a refractometer, and measured as degrees brix.

ph: the pH is a measure of acidity.

Viscosity: the viscosity or consistency of tomato products is affected by the degree of concentration of the tomato, the amount of and extent of degradation of pectine, the size, shape and quality of the pulp, and probably to a lesser extent, by the proteins, sugars and other soluble constituents. The viscosity is measured in Bostwick centimeters by using instruments such as a Bostwick Consistometer.

Quantitative Trait Loci (QTL) Quantitative trait loci refer to genetic loci that control to some degree numerically representable traits that are usually continuously distributed.

Predicted paste bostwick: the predicted paste bostwick is the flow distance of tomato paste diluted to 12 degrees brix and heated prior to evaluation. Dilution to 12 degrees brix for bostwick measurement is a standard method used by industry to evaluate product consistency. The lower the number, the thicker the product and therefore more desirable in consistency oriented products such as catsup. The following formula is usually used to evaluate the predicted paste bostwick: Predicted paste bostwick=$-1.53+(1.64*juice\ brix)+(0.5*juice\ bostwick)$ Determinate tomatoes: varieties that come to fruit all at once, then stop bearing. They are best suited for commercial growing since they can be harvested all at once.

Relative maturity: relative maturity is an indication of time until a tomato genotype is ready for harvest. A genotype is ready for harvest when 90% or more of the tomatoes are ripe.

Semi-erect habit: a semi-erect plant has a combination of lateral and upright branching and has an intermediate type habit between a prostate plant habit, having laterally growing branching with fruits most of the time on the ground and an erect plant habit with branching going straight up with fruit being off the ground.

Deep globe shape: a tomato fruit being slightly wider than longer but still having a round shape.

Flesh color: the color of the tomato flesh that can range from orange-red to dark red when at ripe stage (harvest maturity).

Uniform ripening: a tomato that ripens uniformly, i.e., that has no green discoloration on the shoulders. The uniform ripening is controlled by a single recessive gene.

DETAILED DESCRIPTION OF THE INVENTION

The present invention discloses new and distinct inbred tomato lines and hybrids of tomato (*Lycopersicon esculentum*). The present invention also discloses methods of making and using such inbred lines and hybrids. In one embodiment, the present invention discloses a new and distinct inbred tomato line, designated 1T247. In one embodiment, the present invention relates to a new and distinct inbred tomato line, designated 1T246. In one embodiment, this invention also discloses tomato hybrids Finishline and Redline [4971].

A cross was made between two Syngenta proprietary lines, one determinate, standard large-fruited beef staking type, and one determinate, beef staking type of smaller fruit size but with the single dominant gene, Sw-5, for Tomato Spotted Wilt Virus (TSWV) resistance. The resulting F1 hybrid was identified as 0901. The F1 was selfed and two lines were developed by pedigree selection, 1T247 and 1T246. The 0901 line was split at the F5 generation creating the two breeding lines, and these were inbred further to the F7 generation and crossed with line FLA 7804 to obtain hybrids Finishline and Redline [4971]. Lines combined the superior size, firmness of the fruit of standard type with the added TSWV resistance. Both lines also have resistance to Fol 1, 2, V, and S. Lines 1T247 and 1T246 are superior due to firmness of the fruit, size, and combining ability Additional characteristics of the tomato inbred lines and hybrid of the instant invention are shown in Tables 1 to 4 below.

The tomato inbred lines and hybrid of the instant invention have shown uniformity and stability for all traits. The inbred lines of the present invention have been self-pollinated and planted for a sufficient number of generations, with careful attention to uniformity of plant type to ensure homozygosity and phenotypic stability. No variant traits have been observed or are expected. In one embodiment, the present invention discloses a method of producing seed of a tomato plant of the present invention comprising: a) growing a plant of the present invention; b) allowing said plant to self-pollinate; c) harvesting seeds from said plant.

The inbred lines of the instant invention have superior characteristics, and provide excellent parental lines in crosses for producing first generation (F1) hybrid tomato. In one embodiment, the present invention also discloses a method of producing a hybrid tomato seed. In one embodiment, the method comprises crossing a plant of an inbred tomato line of the instant invention with a plant of another tomato line. In one embodiment, inbred line 1T247 is crossed with inbred line 1T246 to obtain hybrids Finishline and Redline [4971]. In one embodiment, inbred lines 1T247 and 1T246 are used are male parent or female parent to obtain hybrids Finishline and Redline [4971].

Great care is taken during hybrid seed production to prevent contamination of lots of hybrid seeds with seeds of parent inbred lines, in particular of seeds of the female parent. During the production of the hybrid seed, care is taken to harvest only seeds produced by flowers, which have been cross-pollinated by the pollen of the male parent, while avoiding seeds produced by flowers, which have been self-pollinated. After harvest, grow-out tests are typically conducted to test for the undesired presence of seeds of the parental lines by observing the phenotypic characteristics of the hybrids and corresponding parents. Purity test are also conducted using biochemical and molecular markers. Lots of hybrids seeds, which do not produce satisfying results are not released.

A tomato plant can also be propagated vegetatively. A part of the plant, for example a shoot tissue, is collected, and a new plant is obtained from the part. Such part typically comprises an apical meristem of the plant. The collected part is transferred to a medium allowing development of a plantlet, including for example rooting or development of shoots, or is grafted onto a tomato plant or a rootstock prepared to support growth of shoot tissue. This is achieved using methods well-known in the art. Accordingly, in one embodiment, a method of vegetatively propagating a plant of the present invention comprises collecting a part of a plant according to the present invention, e.g. a shoot tissue, and obtaining a plantlet from said part. In one embodiment, a method of vegetatively propagating a plant of the present invention comprises: a) collecting tissue of a plant of the present invention; b) rooting said proliferated shoots to obtain rooted plantlets. In one embodiment, a method of vegetatively propagating a plant of the present invention comprises: a) collecting tissue of a plant of the present invention; b) cultivating said tissue to obtain proliferated shoots; c) rooting said proliferated shoots to obtain rooted plantlets. In one embodiment, such method further comprises growing a plant from said plantlets. In one embodiment, a fruit is harvested from said plant.

The present invention also contemplates a tomato plant regenerated from a tissue culture of an inbred or hybrid plant of the present invention. As is well known in the art, tissue culture of tomato can be used for the in vitro regeneration of a tomato plant. Kartha, K. K., Gamborg, O. L., Shyluk, J. P., and Constabel, F., Morphogenetic investigations on in vitro leaf cultures of tomato (*Lycopersicon esculentum* Mill. cv. Starfire) and high frequency plant regeneration, Z. Pflanzenphysiol., 77, 292, 1976.

In one embodiment, the present invention discloses a method of producing a tomato fruit. In one embodiment, such method comprises growing a plant of the instant invention to produce a tomato fruit, and harvesting said tomato fruit. In one embodiment, the method further comprises packing said fruit in a suitable container. In one embodiment, the method further comprises shipping said fruit. In one embodiment, a fruit of a tomato plant of the present invention is used in fresh consumption or is processed.

Tables 1 to 4 below disclose additional characteristics of the tomato plants of the present invention.

TABLE 1

Characteristics of inbred tomato line 1T247 (Parent of Hybrid Finishline)
Tomato plants were grown in the open field in Naples, Florida, USA under standard conditions.

| Characteristics | | |
|---|---|---|
| Seedling: anthocyanin coloration of hypocotyl | 1 absent/9 present | 9 |
| Stem: type | 1 very rigid/2 flexible. | 2 |
| Stem: Pubescence | 1 absent/3 few/5 medium/7 strong. | 5 |
| Stem: Number of leaves under the first inflorescence | 3 few/5 medium/7 many. | 5 |
| Stem: Internode length (between the 1st and 3rd inflorescence | 3 short/5 medium/7 long. | 5 |
| Plant: growth type | 1 determinate/2 indeterminate/3 semi-determinate | 1 |
| Plant: height | 1 very low/3 low/5 medium/7 high/9 very high. | 5 |
| Plant: vigour | 3 weak/5 medium/7 strong | 5 |
| Plant: speed of growth (Indeterminate varieties only) | 1 very slow/3 slow/5 medium/7 fast/9 very fast | n/a |
| Leaf: pose/attitude | 3 semi upright/5 horizontal/7 downwards. | 5 |
| Leaf: length | 3 short/5 medium/7 long. | 5 |
| Leaf: width | 3 narrow/5 medium/7 wide. | 5 |
| Leaf: density of the foliage | 3 weak/5 medium/7 strong | 5 |
| Leaf: division of blade (see drawings on Instructions tab) | 1 pinnate/9 bipinnate | ? |
| Leaf: type (see drawings on Instructions tab) | 1 type1/2 type2/3 type3/4 type4 | ? |
| Leaf: intensity of green colour | 1 very light/3 light/5 medium/7 dark/9 very dark | 5 |
| Leaf: anthocyanin coloration of the veins | 1 absent/9 present. | 9 |

TABLE 1-continued

Characteristics of inbred tomato line 1T247 (Parent of Hybrid Finishline)
Tomato plants were grown in the open field in Naples, Florida, USA under standard conditions.

| | | |
|---|---|---|
| Inflorescence: type | 1 single flowering/2 multiflowering. | 2 |
| Peduncle: abscission layer (see drawing on Instructions tab) | 1 absent (jointless)/9 present (jointed) | 9 |
| Flower: fasciation (1st flower of inflorescence) | 1 absent/9 present. | 1 |
| Flower: pubescence of style | 1 absent/9 present. | 1 |
| Flower: color | 1 yellow/2 orange. | 1 |
| Fruit: ribbing at stem end (calyx) | 1 absent or very weak/2 weak/3 strong/4 very strong | 1 |
| Fruit: size | 1 very small/3 small/5 medium/7 large/9 very large (220-250 g) | 8 |
| Fruit: shape in longitudinal section | 1 flattened/2 slightly flattened/3 round/4 rectangular/5 cylindrical/6 heart-shaped/7 obovoid/8 ovoid/9 pear-shaped/10 strongly pear-shaped | 3 |
| Fruit: shape in longitudinal section (Spanish classification) | 1 heartshaped/3 elliptic/5 cylindrical/7 pyramidshaped. | 3 |
| Fruit: shape in transverse section | 1 round/2 angular/3 irregular. | 1 |
| Fruit: ratio size/height | 1 very low/3 low/5 medium/7 high/9 very high. | 5 |
| Fruit: length of pedicel (from abscission layer to calyx) | 3 short/7 long. | 5 |
| Fruit: pedicel area | 1 smooth/3 little globe/5 medium globe/7 high globe. | 5 |
| Fruit: size of pedicel scar | 3 small/5 medium/7 big. | 5 |
| Fruit: shape of peduncular part | 1 smooth/5 slightly ribbed/9 ribbed. | 1 |
| Fruit: size of corky area around pedicel scar | 3 small/5 medium/7 big. | 5 |
| Fruit: shape of pistil scar | 1 pointed/2 starshaped/3 striped/4 irregular. | 2 |
| Fruit: predominant number of locules | 1 two/2 two and three/3 three and four/4 four, five, six/5 more then six | 5 |
| Fruit: predominant number of locules (Spanish classification) | 2 mainly two/3 mainly three/4 mainly four/5 mainly five/6 mainly six or more | n/a |
| Fruit: shape at blossom end (see drawings on Instructions tab) | 1 very indented/3 indented/5 round/7 pointed/9 extreme pointed. | 5 |
| Fruit: size of core (in cross-section) | 3 small/7 big. | 5 |
| Fruit: green shoulder (before maturity) | 1 absent/9 present | 1 |
| Fruit: intensity of green shoulder before maturity. | 1 absent/3 weak/5 medium/7 strong/9 very strong. | 1 |
| Fruit: thickness of pericarp | 3 thin/5 medium/7 thick. | 6 |
| Fruit: color before maturity | 3 lightgreen/5 mediumgreen/7 darkgreen. | 3 |
| Fruit: color at maturity | 1 yellow/2 orange/3 pink/4 red/5 darkred/6 brownred. | 4 |
| Fruit: color of the epidermis at maturity | 1 colorless/2 yellow. | 2 |
| Fruit: color of flesh (at maturity) | 1 yellow/2 orange/3 pink/4 red | 4 |
| Fruit: homogenity of size | 1 heterogene/9 homogene | 7 |
| Fruit: firmness | 1 very soft/3 soft/5 medium/7 firm/9 very firm. | 7 |
| Time of flowering (if grown in the greenhouse, to be observed on 3rd flower of the 2nd truss) | 3 early/5 medium/7 late. | 5 |
| Time of maturity | 1 very early/3 early/5 medium/7 late/9 very late | 6 |

Additional information
Resistances to pests and diseases:

| | | |
|---|---|---|
| Expression of silvering | 0 not tested/1 absent (tol. to silvering)/8 present (susc. to silvering) | 0 |
| *Meloidogyne incognita* | 1 absent/9 present | 1 |
| *Verticillium* race 0 | 1 absent/9 present | 9 |
| *Fusarium oxysporum* f. sp. *lycopersici* race 1 | 1 absent/9 present | 9 |
| *Fusarium oxysporum* f. sp. *lycopersici* race 2 | 1 absent/9 present | 9 |
| *Fusarium oxysporum* f. sp. *lycopersici* race 3 | 1 absent/9 present | 1 |
| *Fusarium oxysporium* f. sp. *radicis lycopersici* | 0 not tested/1 absent/9 present. | 0 |
| *Cladosporium fulvum* group 0 (Indeterminate varieties only) | 0 not tested/1 absent/9 present. | 0 |
| *Cladosporium fulvum* group A (Indeterminate varieties only) | 1 absent/9 present | 0 |
| *Cladosporium fulvum* group B (Indeterminate varieties only) | 1 absent/9 present | 0 |
| *Cladosporium fulvum* group C (Indeterminate varieties only) | 1 absent/9 present | 0 |
| *Cladosporium fulvum* group D (Indeterminate varieties only) | 1 absent/9 present | 0 |
| *Cladosporium fulvum* group E (Indeterminate varieties only) | 1 absent/9 present | 0 |
| TMV race 0 | 0 not tested/1 absent/9 present | 0 |
| Tomato mosaic virus (ToMV) strain 0 | 1 absent/9 present | 1 |
| Tomato mosaic virus (ToMV) strain 1 | 1 absent/9 present | 1 |
| Tomato mosaic virus (ToMV) strain 2 | 1 absent/9 present | 1 |
| Tomato mosaic virus (ToMV) strain 1-2 | 0 not tested/1 absent/9 present | 0 |
| *Stemphylium* spp. | 1 absent/9 present | 9 |
| Tomato Spotted Wilt Virus | 1 absent/9 present | 9 |

Special conditions for the examination of the variety

| | | |
|---|---|---|
| Type of culture: | 1 glasshouse/2 outdoor/3 other . . . | 2 |
| Type of culture | 1 staked/2 semi staked/3 not staked | 1 |
| Main use: | 1 fresh market or garden/2 industrial processing | 1 |
| | If 1 fresh market or garden: 1 single/2 truss/3 other, . . . | 1 |

TABLE 2

Characteristics of inbred tomato line 1T246 (Parent of Hybrid Redline 4971)
Tomato plants were grown in the open field in Naples, Florida, USA under standard conditions.

| Characteristics | | |
|---|---|---|
| Seedling: anthocyanin coloration of hypocotyl | 1 absent/9 present | 9 |
| Stem: type | 1 very rigid/2 flexible. | 2 |
| Stem: Pubescence | 1 absent/3 few/5 medium/7 strong. | 5 |
| Stem: Number of leaves under the first inflorescence | 3 few/5 medium/7 many. | 5 |
| Stem: Internode length (between the 1st and 3rd inflorescence | 3 short/5 medium/7 long. | 5 |
| Plant: growth type | 1 determinate/2 indeterminate/3 semi-determinate | 1 |
| Plant: height | 1 very low/3 low/5 medium/7 high/9 very high. | 5 |
| Plant: vigour | 3 weak/5 medium/7 strong | 5 |
| Plant: speed of growth (Indeterminate varieties only) | 1 very slow/3 slow/5 medium/7 fast/9 very fast | n/a |
| Leaf: pose/attitude | 3 semi upright/5 horizontal/7 downwards. | 5 |
| Leaf: length | 3 short/5 medium/7 long. | 5 |
| Leaf: width | 3 narrow/5 medium/7 wide. | 5 |
| Leaf: density of the foliage | 3 weak/5 medium/7 strong | 5 |
| Leaf: division of blade (see drawings on Instructions tab) | 1 pinnate/9 bipinnate | ? |
| Leaf: type (see drawings on Instructions tab) | 1 type1/2 type2/3 type3/4 type4 | ? |
| Leaf: intensity of green colour | 1 very light/3 light/5 medium/7 dark/9 very dark | 5 |
| Leaf: anthocyanin coloration of the veins | 1 absent/9 present. | 9 |
| Inflorescence: type | 1 single flowering/2 multiflowering. | 2 |
| Peduncle: abscission layer (see drawing on Instructions tab) | 1 absent (jointless)/9 present (jointed) | 9 |
| Flower: fasciation (1st flower of inflorescence) | 1 absent/9 present. | 1 |
| Flower: pubescence of style | 1 absent/9 present. | 1 |
| Flower: color | 1 yellow/2 orange. | 1 |
| Fruit: ribbing at stem end (calyx) | 1 absent or very weak/2 weak/3 strong/4 very strong | 1 |
| Fruit: size | 1 very small/3 small/5 medium/7 large/9 very large (220-250 g) | 8 |
| Fruit: shape in longitudinal section | 1 flattened/2 slightly flattened/3 round/4 rectangular/5 cylindrical/6 heart-shaped/7 obovoid/8 ovoid/9 pear-shaped/10 strongly pear-shaped | 3 |
| Fruit: shape in longitudinal section (Spanish classification) | 1 heartshaped/3 elliptic/5 cylindrical/7 pyramidshaped. | 3 |
| Fruit: shape in transverse section | 1 round/2 angular/3 irregular. | 1 |
| Fruit: ratio size/height | 1 very low/3 low/5 medium/7 high/9 very high. | 5 |
| Fruit: length of pedicel (from abscission layer to calyx) | 3 short/7 long. | 5 |
| Fruit: pedicel area | 1 smooth/3 little globe/5 medium globe/7 high globe. | 5 |
| Fruit: size of pedicel scar | 3 small/5 medium/7 big. | 5 |
| Fruit: shape of peduncular part | 1 smooth/5 slightly ribbed/9 ribbed. | 1 |
| Fruit: size of corky area around pedicel scar | 3 small/5 medium/7 big. | 5 |
| Fruit: shape of pistil scar | 1 pointed/2 starshaped/3 striped/4 irregular. | 2 |
| Fruit: predominant number of locules | 1 two/2 two and three/3 three and four/4 four, five, six/5 more then six | 5 |
| Fruit: predominant number of locules (Spanish classification) | 2 mainly two/3 mainly three/4 mainly four/5 mainly five/6 mainly six or more | n/a |
| Fruit: shape at blossom end (see drawings on Instructions tab) | 1 very indented/3 indented/5 round/7 pointed/9 extreme pointed. | 5 |
| Fruit: size of core (in cross-section) | 3 small/7 big. | 5 |
| Fruit: green shoulder (before maturity) | 1 absent/9 present | 1 |
| Fruit: intensity of green shoulder before maturity. | 1 absent/3 weak/5 medium/7 strong/9 very strong. | 1 |
| Fruit: thickness of pericarp | 3 thin/5 medium/7 thick. | 6 |
| Fruit: color before maturity | 3 lightgreen/5 mediumgreen/7 darkgreen. | 3 |
| Fruit: color at maturity | 1 yellow/2 orange/3 pink/4 red/5 darkred/6 brownred. | 4 |
| Fruit: color of the epidermis at maturity | 1 colorless/2 yellow. | 2 |
| Fruit: color of flesh (at maturity) | 1 yellow/2 orange/3 pink/4 red | 4 |
| Fruit: homogenity of size | 1 heterogene/9 homogene | 7 |
| Fruit: firmness | 1 very soft/3 soft/5 medium/7 firm/9 very firm. | 7 |
| Time of flowering (if grown in the greenhouse, to be observed on 3rd flower of the 2nd truss) | 3 early/5 medium/7 late. | 5 |
| Time of maturity | 1 very early/3 early/5 medium/7 late/9 very late | 6 |
| Additional information | | |
| Resistances to pests and diseases: | | |
| Expression of silvering | 0 not tested/1 absent (tol. to silvering)/8 present (susc. to silvering) | 0 |
| *Meloidogyne incognita* | 1 absent/9 present | 1 |
| *Verticillium* race 0 | 1 absent/9 present | 9 |
| *Fusarium oxysporum* f. sp. *lycopersici* race 1 | 1 absent/9 present | 9 |
| *Fusarium oxysporum* f. sp. *lycopersici* race 2 | 1 absent/9 present | 9 |
| *Fusarium oxysporum* f. sp. *lycopersici* race 3 | 1 absent/9 present | 1 |
| *Fusarium oxysporium* f. sp. *radicis lycopersici* | 0 not tested/1 absent/9 present. | 0 |
| *Cladosporium fulvum* group 0 (Indeterminate varieties only) | 0 not tested/1 absent/9 present. | 0 |
| *Cladosporium fulvum* group A (Indeterminate varieties only) | 1 absent/9 present | 0 |
| *Cladosporium fulvum* group B (Indeterminate varieties only) | 1 absent/9 present | 0 |
| *Cladosporium fulvum* group C (Indeterminate varieties only) | 1 absent/9 present | 0 |
| *Cladosporium fulvum* group D (Indeterminate varieties only) | 1 absent/9 present | 0 |
| *Cladosporium fulvum* group E (Indeterminate varieties only) | 1 absent/9 present | 0 |
| TMV race 0 | 0 not tested/1 absent/9 present | 0 |
| Tomato mosaic virus (ToMV) strain 0 | 1 absent/9 present | 1 |

TABLE 2-continued

Characteristics of inbred tomato line 1T246 (Parent of Hybrid Redline 4971)
Tomato plants were grown in the open field in Naples, Florida, USA under standard conditions.

| | | |
|---|---|---|
| Tomato mosaic virus (ToMV) strain 1 | 1 absent/9 present | 1 |
| Tomato mosaic virus (ToMV) strain 2 | 1 absent/9 present | 1 |
| Tomato mosaic virus (ToMV) strain 1-2 | 0 not tested/1 absent/9 present | 0 |
| *Stemphylium* spp. | 1 absent/9 present | 9 |
| Tomato Spotted Wilt Virus | 1 absent/9 present | 9 |
| Special conditions for the examination of the variety | | |
| Type of culture: | 1 glasshouse/2 outdoor/3 other . . . | 2 |
| Type of culture | 1 staked/2 semi staked/3 not staked | 1 |
| Main use: | 1 fresh market or garden/2 industrial processing | 1 |
| | If 1 fresh market or garden: 1 single/2 truss/3 other, . . . | 1 |

TABLE 3

Characteristics of tomato hybrid Finishline)
Tomato plants were grown in the open field in Naples, Florida, USA under standard conditions.

| Characteristics | | |
|---|---|---|
| Seedling: anthocyanin coloration of hypocotyl | 1 absent/9 present | 9 |
| Stem: type | 1 very rigid/2 flexible. | 2 |
| Stem: Pubescence | 1 absent/3 few/5 medium/7 strong. | 5 |
| Stem: Number of leaves under the first inflorescence | 3 few/5 medium/7 many. | 5 |
| Stem: Internode length (between the 1st and 3rd inflorescence | 3 short/5 medium/7 long. | 5 |
| Plant: growth type | 1 determinate/2 indeterminate/3 semi-determinate | 1 |
| Plant: height | 1 very low/3 low/5 medium/7 high/9 very high. | 6 |
| Plant: vigour | 3 weak/5 medium/7 strong | 5 |
| Plant: speed of growth (Indeterminant varieties only) | 1 very slow/3 slow/5 medium/7 fast/9 very fast | 5 |
| Leaf: pose/attitude | 3 semi upright/5 horizontal/7 downwards. | 5 |
| Leaf: length | 3 short/5 medium/7 long. | 5 |
| Leaf: width | 3 narrow/5 medium/7 wide. | 5 |
| Leaf: density of the foliage | 3 weak/5 medium/7 strong | 6 |
| Leaf: division of blade (see drawings on Instructions tab) | 1 pinnate/9 bipinnate | 9 |
| Leaf: type (see drawings on Instructions tab) | 1 type1/2 type2/3 type3/4 type4 | 1 |
| Leaf: intensity of green colour | 1 very light/3 light/5 medium/7 dark/9 very dark | 5 |
| Leaf: anthocyanin coloration of the veins | 1 absent/9 present. | 9 |
| Inflorescence: type | 1 single flowering/2 multiflowering. | 2 |
| Peduncle: abscission layer (see drawing on Instructions tab) | 1 absent (jointless)/9 present (jointed) | 9 |
| Flower: fasciation (1st flower of inflorescence) | 1 absent/9 present. | 9 |
| Flower: pubescence of style | 1 absent/9 present. | 9 |
| Flower: color | 1 yellow/2 orange. | 1 |
| Fruit: ribbing at stem end (calyx) | 1 absent or very weak/2 weak/3 strong/4 very strong | 2 |
| Fruit: size | 1 very small/3 small/5 medium/7 large/9 very large (250 g) | 8 |
| Fruit: shape in longitudinal section 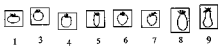 | 1 flattened/2 slightly flattened/3 round/4 rectangular/5 cylindrical/6 heart-shaped/7 obovoid/8 ovoid/9 pear-shaped/10 strongly pear-shaped | 3 |
| Fruit: shape in longitudinal section (Spanish classification) | 1 heartshaped/3 elliptic/5 cylindrical/7 pyramidshaped. | 3 |
| Fruit: shape in transverse section | 1 round/2 angular/3 irregular. | 1 |
| Fruit: ratio size/height | 1 very low/3 low/5 medium/7 high/9 very high. | 5 |
| Fruit: length of pedicel (from abscission layer to calyx) | 3 short/7 long. | 5 |
| Fruit: pedicel area | 1 smooth/3 little globe/5 medium globe/7 high globe. | 5 |
| Fruit: size of pedicel scar | 3 small/5 medium/7 big. | 5 |
| Fruit: shape of peduncular part | 1 smooth/5 slightly ribbed/9 ribbed. | 1 |
| Fruit: size of corky area around pedicel scar | 3 small/5 medium/7 big. | 5 |
| Fruit: shape of pistil scar | 1 pointed/2 starshaped/3 striped/4 irregular. | 3 |
| Fruit: predominant number of locules | 1 two/2 two and three/3 three and four/4 four, five, six/5 more then six | 5 |
| Fruit: predominant number of locules (Spanish classification) | 2 mainly two/3 mainly three/4 mainly four/5 mainly five/6 mainly six or more | 4 |
| Fruit: shape at blossom end (see drawings on Instructions tab) | 1 very indented/3 indented/5 round/7 pointed/9 extreme pointed. | 5 |
| Fruit: size of core (in cross-section) | 3 small/7 big. | 5 |
| Fruit: green shoulder (before maturity) | 1 absent/9 present | 1 |
| Fruit: intensity of green shoulder before maturity. | 1 absent/3 weak/5 medium/7 strong/9 very strong. | 1 |
| Fruit: thickness of pericarp | 3 thin/5 medium/7 thick. | 6 |
| Fruit: color before maturity | 3 lightgreen/5 mediumgreen/7 darkgreen. | 3 |
| Fruit: color at maturity | 1 yellow/2 orange/3 pink/4 red/5 darkred/6 brownred. | 4 |
| Fruit: color of the epidermis at maturity | 1 colorless/2 yellow. | 2 |
| Fruit: color of flesh (at maturity) | 1 yellow/2 orange/3 pink/4 red | 4 |

TABLE 3-continued

Characteristics of tomato hybrid Finishline)
Tomato plants were grown in the open field in Naples, Florida, USA under standard conditions.

| | | |
|---|---|---|
| Fruit: homogenity of size | 1 heterogene/9 homogene | 7 |
| Fruit: firmness | 1 very soft/3 soft/5 medium/7 firm/9 very firm. | 7 |
| Time of flowering (if grown in the greenhouse, to be observed on 3rd flower of the 2nd truss) | 3 early/5 medium/7 late. | 5 |
| Time of maturity | 1 very early/3 early/5 medium/7 late/9 very late | 5 |
| Additional information | | |
| Resistances to pests and diseases: | | |
| Expression of silvering | 0 not tested/1 absent (tol. to silvering)/8 present (susc. to silvering) | 0 |
| *Meloidogyne incognita* | 1 absent/9 present | 1 |
| *Verticillium* race 0 | 1 absent/9 present | 9 |
| *Fusarium oxysporum* f. sp. *lycopersici* race 1 | 1 absent/9 present | 9 |
| *Fusarium oxysporum* f. sp. *lycopersici* race 2 | 1 absent/9 present | 9 |
| *Fusarium oxysporum* f. sp. *lycopersici* race 3 | 1 absent/9 present | 9 |
| *Fusarium oxysporium* f. sp. *radicis lycopersici* | 0 not tested/1 absent/9 present. | 0 |
| *Cladosporium fulvum* group 0 (Indeterminate varieties only) | 0 not tested/1 absent/9 present. | 0 |
| *Cladosporium fulvum* group A (Indeterminate varieties only) | 1 absent/9 present | 0 |
| *Cladosporium fulvum* group B (Indeterminate varieties only) | 1 absent/9 present | 0 |
| *Cladosporium fulvum* group C (Indeterminate varieties only) | 1 absent/9 present | 0 |
| *Cladosporium fulvum* group D (Indeterminate varieties only) | 1 absent/9 present | 0 |
| *Cladosporium fulvum* group E (Indeterminate varieties only) | 1 absent/9 present | 0 |
| TMV race 0 | 0 not tested/1 absent/9 present | 1 |
| Tomato mosaic virus (ToMV) strain 0 | 1 absent/9 present | 1 |
| Tomato mosaic virus (ToMV) strain 1 | 1 absent/9 present | 1 |
| Tomato mosaic virus (ToMV) strain 2 | 1 absent/9 present | 1 |
| Tomato mosaic virus (ToMV) strain 1-2 | 0 not tested/1 absent/9 present | 1 |
| *Stemphylium* spp. | 0 not tested/1 absent/9 present | 9 |
| Tomato Spotted Wilt Virus (TSWV) | 1 absent/9 present | 9 |
| Special conditions for the examination of the variety | | |
| Type of culture: | 1 glasshouse/2 outdoor/3 other . . . | 2 |
| Type of culture | 1 staked/2 semi staked/3 not staked | 1 |
| Main use: | 1 fresh market or garden/2 industrial processing | 1 |
| | If 1 fresh market or garden: 1 single/2 truss/3 other, . . . | 1 |

TABLE 4

Characteristics of tomato hybrid Redline [4971]
Tomato plants were grown in the open field in Naples, Florida, USA under standard conditions.

| Characteristics | | |
|---|---|---|
| Seedling: anthocyanin coloration of hypocotyl | 1 absent/9 present | 9 |
| Stem: type | 1 very rigid/2 flexible. | 2 |
| Stem: Pubescence | 1 absent/3 few/5 medium/7 strong. | 5 |
| Stem: Number of leaves under the first inflorescence | 3 few/5 medium/7 many. | 5 |
| Stem: Internode length (between the 1st and 3rd inflorescence | 3 short/5 medium/7 long. | 5 |
| Plant: growth type | 1 determinate/2 indeterminate/3 semi-determinate | 1 |
| Plant: height | 1 very low/3 low/5 medium/7 high/9 very high. | 6 |
| Plant: vigour | 3 weak/5 medium/7 strong | 5 |
| Plant: speed of growth (Indeterminant varieties only) | 1 very slow/3 slow/5 medium/7 fast/9 very fast | 5 |
| Leaf: pose/attitude | 3 semi upright/5 horizontal/7 downwards. | 5 |
| Leaf: length | 3 short/5 medium/7 long. | 5 |
| Leaf: width | 3 narrow/5 medium/7 wide. | 5 |
| Leaf: density of the foliage | 3 weak/5 medium/7 strong | 6 |
| Leaf: division of blade (see drawings on Instructions tab) | 1 pinnate/9 bipinnate | 9 |
| Leaf: type (see drawings on Instructions tab) | 1 type1/2 type2/3 type3/4 type4 | 1 |
| Leaf: intensity of green colour | 1 very light/3 light/5 medium/7 dark/9 very dark | 5 |
| Leaf: anthocyanin coloration of the veins | 1 absent/9 present. | 9 |
| Inflorescence: type | 1 single flowering/2 multiflowering. | 2 |
| Peduncle: abscission layer (see drawing on Instructions tab) | 1 absent (jointless)/9 present (jointed) | 9 |
| Flower: fasciation (1st flower of inflorescence) | 1 absent/9 present. | 9 |
| Flower: pubescence of style | 1 absent/9 present. | 9 |
| Flower: color | 1 yellow/2 orange. | 1 |
| Fruit: ribbing at stem end (calyx) | 1 absent or very weak/2 weak/3 strong/4 very strong | 2 |
| Fruit: size | 1 very small/3 small/5 medium/7 large/9 very large (250 g) | 8 |
| Fruit: shape in longitudinal section 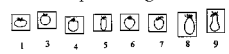 | 1 flattened/2 slightly flattened/3 round/4 rectangular/5 cylindrical/6 heart-shaped/7 obovoid/8 ovoid/9 pear-shaped/10 strongly pear-shaped | 3 |
| Fruit: shape in longitudinal section (Spanish classification) | 1 heartshaped/3 elliptic/5 cylindrical/7 pyramidshaped. | 3 |
| Fruit: shape in transverse section | 1 round/2 angular/3 irregular. | 1 |

TABLE 4-continued

Characteristics of tomato hybrid Redline [4971]
Tomato plants were grown in the open field in Naples, Florida, USA under standard conditions.

| | | |
|---|---|---|
| Fruit: ratio size/height | 1 very low/3 low/5 medium/7 high/9 very high. | 5 |
| Fruit: length of pedicel (from abscission layer to calyx) | 3 short/7 long. | 5 |
| Fruit: pedicel area | 1 smooth/3 little globe/5 medium globe/7 high globe. | 5 |
| Fruit: size of pedicel scar | 3 small/5 medium/7 big. | 5 |
| Fruit: shape of peduncular part | 1 smooth/5 slightly ribbed/9 ribbed. | 1 |
| Fruit: size of corky area around pedicel scar | 3 small/5 medium/7 big. | 5 |
| Fruit: shape of pistil scar | 1 pointed/2 starshaped/3 striped/4 irregular. | 3 |
| Fruit: predominant number of locules | 1 two/2 two and three/3 three and four/4 four, five, six/ 5 more then six | 5 |
| Fruit: predominant number of locules (Spanish classification) | 2 mainly two/3 mainly three/4 mainly four/5 mainly five/6 mainly six or more | 4 |
| Fruit: shape at blossum end (see drawings on Instructions tab) | 1 very indented/3 indented/5 round/7 pointed/9 extreme pointed. | 5 |
| Fruit: size of core (in cross-section) | 3 small/7 big. | 5 |
| Fruit: green shoulder (before maturity) | 1 absent/9 present | 1 |
| Fruit: intensity of green shoulder before maturity. | 1 absent/3 weak/5 medium/7 strong/9 very strong. | 1 |
| Fruit: thickness of pericarp | 3 thin/5 medium/7 thick. | 6 |
| Fruit: color before maturity | 3 lightgreen/5 mediumgreen/7 darkgreen. | 3 |
| Fruit: color at maturity | 1 yellow/2 orange/3 pink/4 red/5 darkred/6 brownred. | 4 |
| Fruit: color of the epidermis at maturity | 1 colorless/2 yellow. | 2 |
| Fruit: color of flesh (at maturity) | 1 yellow/2 orange/3 pink/4 red | 4 |
| Fruit: homogenity of size | 1 heterogene/9 homogene | 7 |
| Fruit: firmness | 1 very soft/3 soft/5 medium/7 firm/9 very firm. | 7 |
| Time of flowering (if grown in the greenhouse, to be observed on 3rd flower of the 2nd truss) | 3 early/5 medium/7 late. | 5 |
| Time of maturity | 1 very early/3 early/5 medium/7 late/9 very late | 5 |

Additional information
Resistances to pests and diseases:

| | | |
|---|---|---|
| Expression of silvering | 0 not tested/1 absent (tol. to silvering)/8 present (susc. to silvering) | 0 |
| *Meloidogyne incognita* | 1 absent/9 present | 1 |
| *Verticillium* race 0 | 1 absent/9 present | 9 |
| *Fusarium oxysporum* f. sp. *lycopersici* race 1 | 1 absent/9 present | 9 |
| *Fusarium oxysporum* f. sp. *lycopersici* race 2 | 1 absent/9 present | 9 |
| *Fusarium oxysporum* f. sp. *lycopersici* race 3 | 1 absent/9 present | 9 |
| *Fusarium oxysporium* f. sp. *radicis lycopersici* | 0 not tested/1 absent/9 present. | 0 |
| *Cladosporium fulvum* group 0 (Indeterminate varieties only) | 0 not tested/1 absent/9 present. | 0 |
| *Cladosporium fulvum* group A (Indeterminate varieties only) | 1 absent/9 present | 0 |
| *Cladosporium fulvum* group B (Indeterminate varieties only) | 1 absent/9 present | 0 |
| *Cladosporium fulvum* group C (Indeterminate varieties only) | 1 absent/9 present | 0 |
| *Cladosporium fulvum* group D (Indeterminate varieties only) | 1 absent/9 present | 0 |
| *Cladosporium fulvum* group E (Indeterminate varieties only) | 1 absent/9 present | 0 |
| TMV race 0 | 0 not tested/1 absent/9 present | 1 |
| Tomato mosaic virus (ToMV) strain 0 | 1 absent/9 present | 1 |
| Tomato mosaic virus (ToMV) strain 1 | 1 absent/9 present | 1 |
| Tomato mosaic virus (ToMV) strain 2 | 1 absent/9 present | 1 |
| Tomato mosaic virus (ToMV) strain 1-2 | 0 not tested/1 absent/9 present | 1 |
| *Stemphylium* spp. | 0 not tested/1 absent/9 present | 9 |
| Tomato Spotted Wilt Virus (TSWV) | 1 absent/9 present | 9 |

Special conditions for the examination of the variety

| | | |
|---|---|---|
| Type of culture: | 1 glasshouse/2 outdoor/3 other . . . | 2 |
| Type of culture | 1 staked/2 semi staked/3 not staked | 1 |
| Main use: | 1 fresh market or garden/2 industrial processing | 1 |
| | If 1 fresh market or garden: 1 single/2 truss/3 other, . . . | 1 |

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed line.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed tomato plants, using transformation methods as described below to incorporate transgenes into the genetic material of the tomato plant(s).

Expression Vectors for Tomato Transformation

Marker Genes—Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., Proc. Natl. Acad. Sci. U.S.A., 80:4803 (1983), Aragao F. J. L., et al., Molecular Breeding 4:6 491-499 (1998). Another commonly used selectable marker gene is the hygromycin phosphotransferase gene which confers resistance to the antibiotic hygromycin. Vanden Elzen et al., Plant Mol. Biol., 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., Plant Physiol. 86:1216 (1988), Jones et al., Mol. Gen. Genet., 210:86 (1987), Svab et al., Plant Mol. Biol. 14:197 (1990), Hille et al., Plant Mol. Biol. 7:171 (1986).

Other selectable marker genes confer resistance to herbicides such as glyphosate, glufosinate or broxynil. Comai et al., Nature 317:741-744 (1985), Gordon-Kamm et al., Plant Cell 2:603-618 (1990) and Stalker et al., Science 242:419-423 (1988), Saker M. M., et al, Biologia Plantarum 40:4 507-514 (1998), Russel, D. R., et al, Plant Cell Report 12:3 165-169 (1993).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., Somatic Cell Mol. Genet. 13:67 (1987), Shah et al., Science 233:478 (1986), Charest et al., Plant Cell Rep. 8:643 (1990).

Another class of marker genes for plant transformation require screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include beta-glucuronidase (GUS), alpha-galactosidase, luciferase and chloramphenicol, acetyltransferase. Jefferson, R. A., Plant Mol. Biol. Rep. 5:387 (1987), Teeri et al., EMBO J. 8:343 (1989), Koncz et al., Proc. Natl. Acad. Sci U.S.A. 84:131 (1987), DeBlock et al., EMBO J. 3:1681 (1984), Grossi M. F., et al., Plant Science 103:2 189-198 (1994), Lewis M. E., Journal of the American Society for Horticultural Science 119:2 361-366 (1994), Zhang et al., Journal of the American Society for Horticultural Science 122:3 300-305 (1997).

Recently, in vivo methods for visualizing GUS activity that do not require destruction of plant tissue have been made available. Molecular Probes publication 2908, Imagene Green_, p. 1-4 (1993) and Naleway et al., J. Cell Biol. 115: 151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., Science 263: 802 (1994). GFP and mutants of GFP may be used as screenable markers.

Promoters—Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in tomato. Optionally, the inducible promoter is operably linked to a nucleotide sequence encoding a signal sequence which is operably linked to a gene for expression in tomato. With an inducible promoter the rate of transcription increases in response to an inducing agent.

Any inducible promoter can be used in the instant invention. See Ward et al., Plant Mol. Biol. 22:361-366 (1993). Exemplary inducible promoters include, but are not limited to, that from the ACEI system which responds to copper (Meft et al., PNAS 90:4567-4571 (1993)); In2 gene from maize which responds to benzenesulfonamide herbicide safeners (Hershey et al., Mol. Gen Genetics 227:229-237 (1991) and Gatz et al., Mol. Gen. Genetics 243:32-38 (1994)) or Tet repressor from Tn10 (Gatz et al., Mol. Gen. Genetics 227: 229-237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., Proc. Natl. Acad. Sci. U.S.A. 88:0421 (1991).

B. Constitutive Promoters

A constitutive promoter is operably linked to a gene for expression in tomato or the constitutive promoter is operably linked to a nucleotide sequence encoding a signal sequence which is operably linked to a gene for expression in tomato.

Many different constitutive promoters can be utilized in the instant invention. Exemplary constitutive promoters include, but are not limited to, the promoters from plant viruses such as the 35S promoter from CaMV (Odell et al., Nature 313:810-812 (1985), Aragao et al., Genetics and Molecular Biology 22:3, 445-449 (1999) and the promoters from such genes as rice actin (McElroy et al., Plant Cell 2:163-171 (1990)); ubiquitin (Christensen et al., Plant Mol. Biol. 12:619-632 (1989) and Christensen et al., Plant Mol. Biol. 18:675-689 (1992)); pEMU (Last et al., Theor. Appl. Genet. 81:581-588 (1991)); MAS (Velten et al., EMBO J. 3:2723-2730 (1984)) and maize H3 histone (Lepetit et al., Mol. Gen. Genetics 231:276-285 (1992) and Atanassova et al., Plant Journal 2 (3): 291-300 (1992)).

The ALS promoter, Xba1/Nco1 fragment 5' to the *Brassica napus* ALS3 structural gene (or a nucleotide sequence similarity to said Xba1/Nco1 fragment), represents a particularly useful constitutive promoter. See PCT application WO96/30530.

C. Tissue-Specific or Tissue-Preferred Promoters

A tissue-specific promoter is operably linked to a gene for expression in tomato.

Optionally, the tissue-specific promoter is operably linked to a nucleotide sequence encoding a signal sequence which is operably linked to a gene for expression in tomato. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., Science 23:476-482 (1983) and Sengupta-Gopalan et al., Proc. Natl. Acad. Sci. U.S.A. 82:3320-3324 (1985)); a leaf-specific and light-induced promoter such as that from cab or rubisco (Simpson et al., EMBO J. 4(11): 2723-2729 (1985) and Timko et al., Nature 318:579-582 (1985)); an anther-specific promoter such as that from LAT52 (Twell et al., Mol. Gen. Genetics 217:240-245 (1989)); a pollen-specific promoter such as that from Zm13 (Guerrero et al., Mol. Gen. Genetics 244:161-168 (1993)) or a microspore-preferred promoter such as that from apg (Twell et al., Sex. Plant Reprod. 6:217-224 (1993).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., Plant Mol. Biol. 20:49 (1992), Close, P. S., Master's Thesis, Iowa State University (1993), Knox, C., et al., "Structure and Organization of Two Divergent Alpha-Amylase Genes from Barley", Plant Mol. Biol. 9:3-17 (1987), Lerner et al., Plant Physiol. 91:124-129 (1989), Fontes et al., Plant Cell 3:483-496 (1991), Matsuoka et al., Proc. Natl. Acad. Sci. 88:834 (1991), Gould et al., J. Cell. Biol. 108:1657 (1989), Creissen et al., Plant J. 2:129 (1991), Kalderon, et al., A short amino acid sequence able to specify nuclear location, Cell 39:499-509 (1984), Steifel, et al., Expression of a maize cell wall hydroxyproline-rich glycoprotein gene in early leaf and root vascular differentiation, Plant Cell 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114:92-6 (1981). According to a preferred embodiment, the transgenic plant provided for commercial production of foreign protein is tomato. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode

A. Plant disease resistance genes. Plant defenses are often activated by specific interaction between the product of a disease resistance gene (R) in the plant and the product of a corresponding avirulence (Avr) gene in the pathogen. A plant line can be transformed with cloned resistance gene to engineer plants that are resistant to specific pathogen strains. See, for example Jones et al., Science 266:789 (1994) (cloning of the tomato Cf-9 gene for resistance to *Cladosporium fulvum*); Martin et al., Science 262:1432 (1993) (tomato Pto gene for resistance to *Pseudomonas syringae* pv. Tomato encodes a protein kinase); Mindrinos et al., Cell 78:1089 (1994) (Arabidopsis RSP2 gene for resistance to *Pseudomonas syingae*).

B. A *Bacillus thuringiensis* protein, a derivative thereof or a synthetic polypeptide modeled thereon. See, for example, Geiser et al., Gene 48:109 (1986), who disclose the cloning and nucleotide sequence of a Bt delta-endotoxin gene. Moreover, DNA molecules encoding delta-endotoxin genes can be purchased from American Type Culture Collection, Manassas, Va., for example, under ATCC Accession Nos. 40098, 67136, 31995 and 31998.

C. A lectin. See, for example, the disclose by Van Damme et al., Plant Molec. Biol. 24:25 (1994), who disclose the nucleotide sequences of several *Clivia miniata* mannose-binding lectin genes.

D. A vitamin-binding protein such as avidin. See PCT application US93/06487, the contents of which are hereby incorporated by reference. The application teaches the use of avidin and avidin homologues as larvicides against insect pests.

E. An enzyme inhibitor, for example, a protease or proteinase inhibitor or an amylase inhibitor. See, for example, Abe et al., J. Biol. Chem. 262:16793 (1987) (nucleotide sequence of rice cysteine proteinase inhibitor), Huub et al., Plant Molec. Biol. 21:985 (1993) (nucleotide sequence of cDNA encoding tobacco proteinase inhibitor I), Sumitani et al., Biosci. Biotech. Biochem. 57:1243 (1993) (nucleotide sequence of *Streptomyces nitrosporeus* alpha-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., Nature 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, J. Biol. Chem. 269:9 (1994) (expression cloning yields DNA coding for insect diuretic hormone receptor), and Pratt et al., Biochem. Biophys. Res. Comm. 163:1243 (1989) (an allostatin is identified in *Diploptera puntata*). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., Gene 116:165 (1992), for disclosure of heterologous expression in plants of a gene coding for a scorpion insectotoxic peptide.

I. An enzyme responsible for a hyper accumulation of a monterpene, a sesquiterpene, a steroid, hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23:691 (1993), who teach the nucleotide sequence of a cDNA encoding tobacco hookworm chitinase, and Kawalleck et al., Plant Molec. Biol. 21:673 (1993), who provide the nucleotide sequence of the parsley ubi4-2 polyubiquitin gene.

K. A molecule that stimulates signal transduction. For example, see the disclosure by Botella et al., Plant Molec. Biol. 24:757 (1994), of nucleotide sequences for mung tomato calmodulin cDNA clones, and Griess et al., Plant Physiol. 104:1467 (1994), who provide the nucleotide sequence of a maize calmodulin cDNA clone.

L. A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance), the respective contents of which are hereby incorporated by reference.

M. A membrane permease, a channel former or a channel blocker. For example, see the disclosure of Jaynes et al., Plant Sci 89:43 (1993), of heterologous expression of a cecropin-beta, lytic peptide analog to render transgenic tobacco plants resistant to *Pseudomonas solanacearum.*

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. rev. Phytopathol. 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., Nature 366:469 (1993), who show that transgenic plants expressing recombinant antibody genes are protected from virus attack.

Q. A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See Lamb et al., Bio/Technology 10:1436 (1992). The cloning and characterization of a gene which encodes a tomato endopolygalacturonase-inhibiting protein is described by Toubart et al., Plant J. 2:367 (1992).

R. A development-arrestive protein produced in nature by a plant. For example, Logemann et al., Bioi/Technology 10:305 (1992), have shown that transgenic plants expressing the barley ribosome-inactivating gene have an increased resistance to fungal disease.

2. Genes that Confer Resistance to a Herbicide, for Example

A. A herbicide that inhibits the growing point or meristem, such as an imidazalinone or a sulfonylurea. Exemplary genes in this category code for mutant ALS and AHAS enzyme as described, for example, by Lee et al., EMBO J. 7:1241 (1988), and Miki et al., Theor. Appl. Genet. 80:449 (1990), respectively.

B. Glyphosate (resistance impaired by mutant 5-enolpyruvl-3-phosphikimate synthase (EPSP) and aroA genes, respectively) and other phosphono compounds such as glufosinate (phosphinothricin acetyl transferase, PAT and *Streptomyces hygroscopicus* phosphinothricin-acetyl transferase, bar, genes), and pyridinoxy or phenoxy propionic acids and cycloshexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. See also Russel, D. R., et al, Plant Cell Report 12:3 165-169 (1993). The nucleotide sequence of a phosphinothricin-acetyl-transferase gene is provided in European application No. 0 242 246 to Leemans et al., DeGreef et al., Bio/Technology 7:61 (1989), describe the production of transgenic plants that express chimeric bar genes coding for phosphinothricin acetyl transferase activity. Exemplary of genes conferring resistance to phenoxy propionic acids and cycloshexones, such as sethoxydim and haloxyfop are the Acc1-S1, Acc1-S2 and Acc1-S3 genes described by Marshall et al., Theor. Appl. Genet. 83:435 (1992).

C. A herbicide that inhibits photosynthesis, such as a triazine (psbA and gs+ genes) and a benzonitrile (nitrilase gene). Przibilla et al., Plant Cell 3:169 (1991), describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., Biochem. J. 285:173 (1992).

3. Genes That Confer or Contribute to a Value-Added Trait, Such as

A. Delayed and attenuated symptoms to Tomato Golden Mosaic Geminivirus (BGMV), for example by transforming a plant with antisense genes from the Brazilian BGMV. See Arago et al., Molecular Breeding. 1998, 4: 6, 491-499.

B. Increased the tomato content in Methionine by introducing a transgene coding for a Methionine rich storage albumin (2S-albumin) from the Brazil nut as described in Arago et al., Genetics and Molecular Biology. 1999, 22: 3, 445-449.

Numerous methods for plant transformation have been developed, including biological and physical, plant transformation protocols. See, for example, Miki et al., "Procedures for Introducing Foreign DNA into Plants" in Methods in Plant Molecular Biology and Biotechnology, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick B. R. and Thompson, J. E. Eds. (CRC Press, Inc., Boca Raton, 1993) pages 89-119.

A. Agrobacterium-Mediated Transformation

One method for introducing an expression vector into plants is based on the natural transformation system of Agrobacterium. See, for example, Horsch et al., Science 227:1229 (1985). McClean, P., et al. Plant Cell Tissue Org. Cult. 24(2, February), 131-138 (1991), Lewis et al., Journal of the American Society for Horticultural Science, 119:2, 361-366 (1994), Zhang, Z., et al. J. Amer. Soc. Hort. Sci. 122(3): 300-305 (1997). A. tumefaciens and A. rhizogenes are plant pathogenic soil bacteria which genetically transform plant cells. The Ti and Ri plasmids of A. tumefaciens and A. rhizogenes, respectively, carry genes responsible for genetic transformation of the plant. See, for example, Kado, C. I., Crit. Rev. Plant Sci. 10:1 (1991). Descriptions of Agrobacterium vector systems and methods for Agrobacterium-mediated gene transfer are provided by Gruber et al., supra, Miki et al., supra, and Moloney et al., Plant Cell Reports 8:238 (1989). See also, U.S. Pat. No. 5,591,616 issued Jan. 7, 1997.

B. Direct Gene Transfer

Despite the fact the host range for Agrobacterium-mediated transformation is broad, some major cereal or vegetable crop species and gymnosperms have generally been recalcitrant to this mode of gene transfer, even though some success has recently been achieved in rice and corn. Hiei et al., The Plant Journal 6:271-282 (1994) and U.S. Pat. No. 5,591,616 issued Jan. 7, 1997. Several methods of plant transformation, collectively referred to as direct gene transfer, have been developed as an alternative to Agrobacterium-mediated transformation.

A generally applicable method of plant transformation is microprojectile-mediated transformation wherein DNA is carried on the surface of microprojectiles measuring 1 to 4 im. The expression vector is introduced into plant tissues with a biolistic device that accelerates the microprojectiles to speeds of 300 to 600 m/s which is sufficient to penetrate plant cell walls and membranes. Russell, D. R., et al. Pl. Cell. Rep. 12(3, January), 165-169 (1993), Aragao, F. J. L., et al. Plant Mol. Biol. 20(2, October), 357-359 (1992), Aragao Theor. Appl. Genet. 93:142-150 (1996), Kim, J.; Minamikawa, T. Plant Science 117: 131-138 (1996), Sanford et al., Part. Sci. Technol. 5:27 (1987), Sanford, J. C., Trends Biotech. 6:299 (1988), Klein et al., Bio/Technology 6:559-563 (1988), Sanford, J. C., Physiol Plant 7:206 (1990), Klein et al., Biotechnology 10:268 (1992)

Another method for physical delivery of DNA to plants is sonication of target cells. Zhang et al., Bio/Technology 9:996 (1991). Alternatively, liposome or spheroplast fusion have been used to introduce expression vectors into plants. Deshayes et al., EMBO J., 4:2731 (1985), Christou et al., Proc Natl. Acad. Sci. U.S.A. 84:3962 (1987). Direct uptake of DNA into protoplasts using $CaCl_2$ precipitation, polyvinyl alcohol or poly-L-ornithine have also been reported. Hain et al., Mol. Gen. Genet. 199:161 (1985) and Draper et al., Plant Cell Physiol. 23:451 (1982). Electroporation of protoplasts and whole cells and tissues have also been described. Saker, M.; Kuhne, T. Biologia Plantarum 40(4): 507-514 (1997/98), Donn et al., In Abstracts of VIIth International Congress on Plant Cell and Tissue Culture IAPTC, A2-38, p 53 (1990); D'Halluin et al., Plant Cell 4:1495-1505 (1992) and Spencer et al., Plant Mol. Biol. 24:51-61 (1994).

Following transformation of tomato target tissues, expression of the above-described selectable marker genes allows for preferential selection of transformed cells, tissues and/or plants, using regeneration and selection methods now well known in the art. The foregoing methods for transformation would typically be used for producing a transgenic line. The transgenic line could then be crossed, with another (nontransformed or transformed) line, in order to produce a new transgenic tomato line. Alternatively, a genetic trait which has been engineered into a particular tomato cultivar using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

When the term garden tomato plant, cultivar or tomato line is used in the context of the present invention, this also includes any single gene conversions of that cultivar or line. The term single gene converted plant as used herein refers to those garden tomato plants which are developed by a plant breeding technique called backcrossing wherein essentially all of the desired morphological and physiological characteristics of a cultivar are recovered in addition to the single gene transferred into the line via the backcrossing technique. Backcrossing methods can be used with the present invention to improve or introduce a characteristic into the line. The term backcrossing as used herein refers to the repeated crossing of a hybrid progeny back to one of the parental tomato plants for that line. The parental tomato plant which contributes the gene for the desired characteristic is termed the nonrecurrent or donor parent. This terminology refers to the fact that the nonrecurrent parent is used one time in the backcross protocol and therefore does not recur. The parental tomato plant to which the gene or genes from the nonrecurrent parent are transferred is known as the recurrent parent as it is used for several rounds in the backcrossing protocol (Poehlman &

Sleper, 1994; Fehr, 1987). In a typical backcross protocol, the original cultivar of interest (recurrent parent) is crossed to a second line (nonrecurrent parent) that carries the single gene of interest to be transferred. The resulting progeny from this cross are then crossed again to the recurrent parent and the process is repeated until a garden tomato plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original line. To accomplish this, a single gene of the recurrent cultivar is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new line but that can be improved by backcrossing techniques. Single gene traits may or may not be transgenic, examples of these traits include but are not limited to, herbicide resistance (such as bar or pat genes), resistance for bacterial, fungal, or viral disease such as gene I used for BCMV resistance), insect resistance, enhanced nutritional quality (such as 2s albumine gene), industrial usage, agronomic qualities such as the "persistent green gene", yield stability and yield enhancement. These genes are generally inherited through the nucleus. Some other single gene traits are described in U.S. Pat. Nos. 5,777,196; 5,948,957 and 5,969,212, the disclosures of which are specifically hereby incorporated by reference.

All references cited herein are incorporated by reference in the application in their entireties.

The foregoing invention has been described in detail by way of illustration and example for purposes of clarity and understanding. However, it will be obvious that certain changes and modifications such as single gene modifications and mutations, somaclonal variants, variant individuals selected from large populations of the plants of the instant inbred and the like may be practiced within the scope of the invention, as limited only by the scope of the appended claims.

Deposit

Applicants have made a deposit of at least 2500 seeds of inbred tomato lines 1T247 and 1T246 with the American Type Culture Collection (ATCC), Manassas, Va., 20110-2209 U.S.A., ATCC Deposit Nos: PTA-9423 and PTA-9422, respectively. These deposits will be maintained in the ATCC depository, which is a public depository, for a period of 30 years, or 5 years after the most recent request, or for the effective life of the patent, whichever is longer, and will be replaced if it becomes nonviable during that period. Additionally, Applicants have satisfied all the requirements of 37 C.F.R. §§1.801-1.809, including providing an indication of the viability of the sample. Applicants impose no restrictions on the availability of the deposited material from the ATCC; however, Applicants have no authority to waive any restrictions imposed by law on the transfer of biological material or its transportation in commerce. Applicants do not waive any infringement of its rights granted under this patent or under the Plant Variety Protection Act (7 USC 2321 et seq.).

What is claimed is:

1. Seed of inbred tomato line 1T247, representative seed of said tomato line having been deposited under ATCC Accession No. PTA-9423.

2. A tomato plant, or a part thereof, produced by growing the seed of claim 1.

3. Pollen or an ovule of the plant of claim 2.

4. A fruit of the plant of claim 2.

5. A tissue culture of regenerable cells of a plant of inbred tomato line 1T247, wherein the tissue regenerates plants having all the morphological and physiological characteristics of a plant of inbred tomato line 1T247, representative seeds having been deposited under ATCC Accession No. PTA-9423.

6. The tissue culture of claim 5, selected from the group consisting of protoplast and calli, wherein the regenerable cells are produced from meristematic cells, leaves, pollen, embryo, root, root tips, stems, anther, flowers, seeds.

7. A tomato plant regenerated from the tissue culture of claim 5, wherein the regenerated plant has all the morphological and physiological characteristics of a plant of inbred tomato line 1T247, representative seeds having been deposited under ATCC Accession No. PTA-9423.

8. A method for producing a hybrid tomato seed comprising crossing a first parent tomato plant with a second parent tomato plant and harvesting the resultant hybrid tomato seed, wherein said first or second parent tomato plant is the tomato plant of claim 2.

9. A method of producing an herbicide resistant tomato plant, an insect resistant tomato plant or a disease resistant tomato plant comprising transforming the tomato plant of claim 2 with a transgene that confers herbicide resistance, insect resistance or resistance to bacterial, fungal or viral disease.

10. An herbicide resistant tomato plant produced by the method of claim 9.

11. The tomato plant of claim 10, wherein the transgene confers resistance to an herbicide selected from the group consisting of imidazolinone, sulfonylurea glyphosate, glufosinate, L-phosphinothricin, triazine and benzonitrile.

12. An insect resistant tomato plant produced by the method of claim 9.

13. The tomato plant of claim 12, wherein the transgene encodes a *Bacillus thuringiensis* protein.

14. A disease resistant tomato plant produced by the method of claim 9.

15. A method of producing a tomato fruit comprising:
   a) growing the tomato plant of claim 2 to produce a tomato fruit, and
   b) harvesting said tomato fruit.

16. The method according to claim 15, further comprising packing said tomato fruit in a container.

17. A method of producing a tomato seed comprising:
   a) growing the tomato plant of claim 2 to produce a tomato seed, and
   b) harvesting said tomato seed.

* * * * *